US00PP22507P2

(12) United States Plant Patent
Domen

(10) Patent No.: US PP22,507 P2
(45) Date of Patent: Feb. 21, 2012

(54) ***CORNUS* PLANT NAMED 'EVA'**

(50) Latin Name: *Cornus kousa*
Varietal Denomination: Eva

(75) Inventor: Adrianus Johannes Marie Domen, Wernhout (NL)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 12/806,250

(22) Filed: Aug. 7, 2010

(51) Int. Cl.
*A01H 5/00* (2006.01)

(52) U.S. Cl. ..... Plt./220

(58) Field of Classification Search ..... Plt./220
See application file for complete search history.

(56) References Cited

OTHER PUBLICATIONS

UPOV-ROM GTITM, Plant Variety Database, 2011,/01, GTI Jouve Retrieval Software, Citation for plant 'Eva'.*

* cited by examiner

*Primary Examiner* — Susan McCormick Ewoldt
(74) *Attorney, Agent, or Firm* — C. A. Whealy

(57) ABSTRACT

A new and distinct cultivar of *Cornus* plant named 'Eva', characterized by its compact and mounded plant habit; freely branching habit; dense and bushy appearance; and white and green variegated leaves with red purple-colored apices; leaves becoming red in color in the autumn.

3 Drawing Sheets

Botanical designation: *Cornus kousa.*
Cultivar denomination: 'EVA'.

BACKGROUND OF THE INVENTION

The present invention relates to a new and distinct cultivar of *Cornus* plant, commercially produced as an ornamental shrub, botanically known as *Cornus kousa* and hereinafter referred to by the name 'Eva'.

The new *Cornus* plant is a product of a planned breeding program conducted by the Inventor in Wernhout, The Netherlands. The objective of the breeding program was to develop new *Cornus* plants with improved growth habit and unique leaf coloration.

The new *Cornus* plant originated from an open-pollination in 2003 of an unnamed selection of *Cornus kousa,* not patented, as the female, or seed, parent with an unknown selection of *Cornus kousa.* The new *Cornus* plant was discovered and selected by the Inventor from within the progeny of the stated open-pollination in a controlled environment in Wernhout, The Netherlands in 2003.

Asexual reproduction of the new *Cornus* plant by softwood cuttings in a controlled environment in Lottum, The Netherlands since 2005, has shown that the unique features of this new *Cornus* plant are stable and reproduced true to type in successive generations.

SUMMARY OF THE INVENTION

Plants of the new *Cornus* have not been observed under all possible conditions. The phenotype may vary somewhat with variations in environment such as temperature and light intensity without, however, any variance in genotype.

The following traits have been repeatedly observed and are determined to be the unique characteristics of 'Eva'. These characteristics in combination distinguish 'Eva' as a new and distinct cultivar of *Cornus* plant:

1. Compact and mounded plant habit.
2. Freely branching habit; dense and bushy appearance.
3. White and green variegated leaves with red purple-colored apices; leaves becoming red in color in the autumn.

Plants of the new *Cornus* differ from plants of the female parent selection in the following characteristics:

1. Plants of the new *Cornus* are more compact and denser than plants of the female parent selection.
2. Plants of the new *Cornus* and the female parent selection differ in leaf color as plants of the female parent selection have green-colored leaves.

Plants of the new *Cornus* can also be compared to plants of *Cornus kousa* 'Snowboy', not patented. Plants of the new *Cornus* differ from plants of 'Snowboy' in the following characteristics:

1. Plants of the new *Cornus* are more compact than plants of 'Snowboy'.
2. Plants of the new *Cornus* are denser and bushier than plants of 'Snowboy'.
3. Plants of the new *Cornus* are stronger and more durable than plants of 'Snowboy'.

BRIEF DESCRIPTION OF THE PHOTOGRAPHS

The accompanying colored photographs illustrate the overall appearance of the new *Cornus* plant showing the colors as true as it is reasonably possible to obtain in colored reproductions of this type. Colors in the photographs may differ slightly from the color values cited in the detailed botanical description which accurately describe the colors of the new *Cornus* plant.

The photograph on the first sheet comprises a side perspective view of a typical plant of 'Eva' grown in a container.

The photograph on the second sheet is a close-up view of a typical leaf of 'Eva'.

The photograph on the third sheet is a close-up view of a typical leaf of 'Eva' with fall coloration.

DETAILED BOTANICAL DESCRIPTION

The aforementioned photographs and following observations, measurements and values describe plants grown in three-liter containers in Lottum, The Netherlands, under commercial practice in an outdoor nursery. During the production of the plants, day temperatures ranged from 8° C. to 23° C. and night temperatures ranged from 1° C. to 15° C. Plants were three years old when the photographs and description were taken. In the following description, color references are made to The Royal Horticultural Society Colour Chart, 2007 Edition, except where general terms of ordinary dictionary significance are used.

Botanical classification: *Cornus kousa* 'Eva'.

Parentage:

*Female, or seed, parent.*—Unnamed selection of *Cornus kousa,* not patented.

*Male, or pollen parent.*—Unknown selection of *Cornus kousa,* not patented.

Plant description:

*Root description.*—Fine, fibrous; grey to black in color.

*Rooting habit.*—Freely branching; dense.

*Plant form/habit.*—Compact, upright, broadly spreading and mounding deciduous shrub; outwardly spreading form; freely branching habit, about 28 lateral branches per plant; dense and bushy appearance.

*Plant height.*—About 28 cm.

*Plant width* (*spread*).—About 40.5 cm.

*Lateral branches.*—Length: About 10.5 cm. Diameter: About 2 mm. Internode length: About 2.7 cm. Strength: Strong. Texture: Smooth, glabrous. Color, developing stems: Close to N186C. Color, fully developed stems: Close to 195A becoming closer to 199B to 199C.

Foliage description:

*Arrangement.*—Opposite, simple.

*Length.*—About 6.4 cm.

*Width.*—About 2.6 cm.

*Shape.*—Narrowly elliptic to narrowly ovate.

*Apex.*—Acuminate.

*Base.*—Attenuate.

*Margin.*—Entire; undulate.

*Texture, upper and lower surfaces.*—Smooth, glabrous.

*Venation pattern.*—Pinnate.

*Color.*—Developing leaves, upper surface: Center, close to 137B; towards the margins, close to 150D; towards the apex, close to 58A to 63B. Developing leaves, lower surface: Center, close to 137D; towards the margins, close to 150D; towards the apex, close to 63C to 64D. Fully expanded leaves, upper surface: Center, between 137B to 137C and 191A with scattered random blotches, close to 191C to 191D; towards the margins, close to 155D to NN155A; towards the apex, close to 58A to 63B; venation, close to 145C to 145D. During the autumn, center color becomes closer to 187A and towards the margins and apex, close to 63A to 63B to 184C to 184D. Fully expanded leaves, lower surface: Center, close to 191A with scattered random blotches, close to 191B; towards the margins, close to 155D; towards the apex, close to 63C to 64D; venation, close to 148D.

*Petiole.*—Length: About 2 mm. Diameter: About 1.2 mm. Texture, upper and lower surfaces: Smooth, glabrous. Color, upper and lower surfaces: Close to 145A to 145B.

Flower description: Flower initiation and development has not been observed on plants of the new *Cornus.*

Disease/pest resistance: Plants of the new *Cornus* have not been noted to be resistant to pathogens and pests common to *Cornus.*

Temperature tolerance: Plants of the new *Cornus* have been observed to tolerate high temperatures of about 35° C. and to be hardy to USDA Hardiness Zone 6.

It is claimed:

1. A new and distinct *Cornus* plant named 'Eva' as illustrated and described.

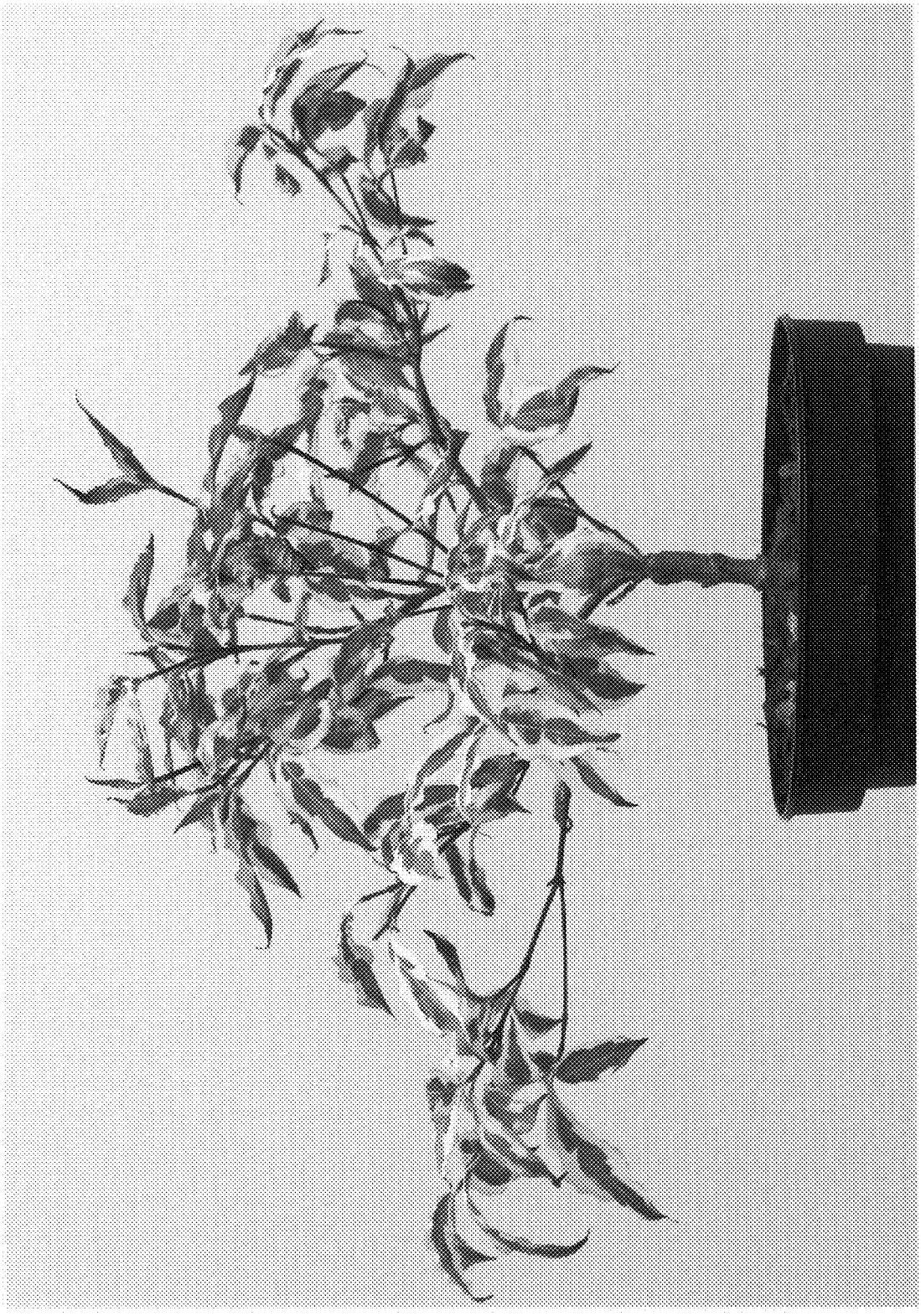

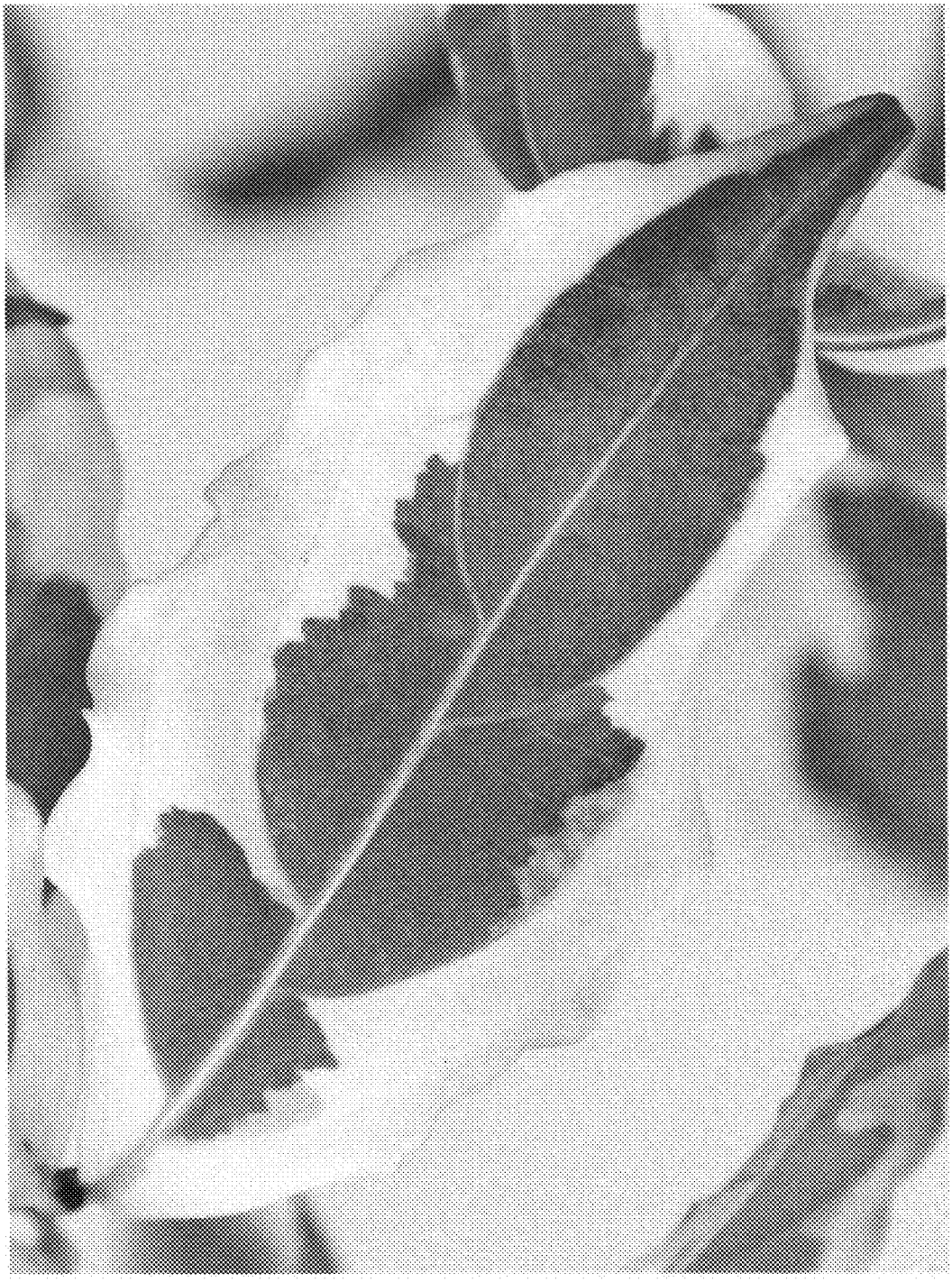

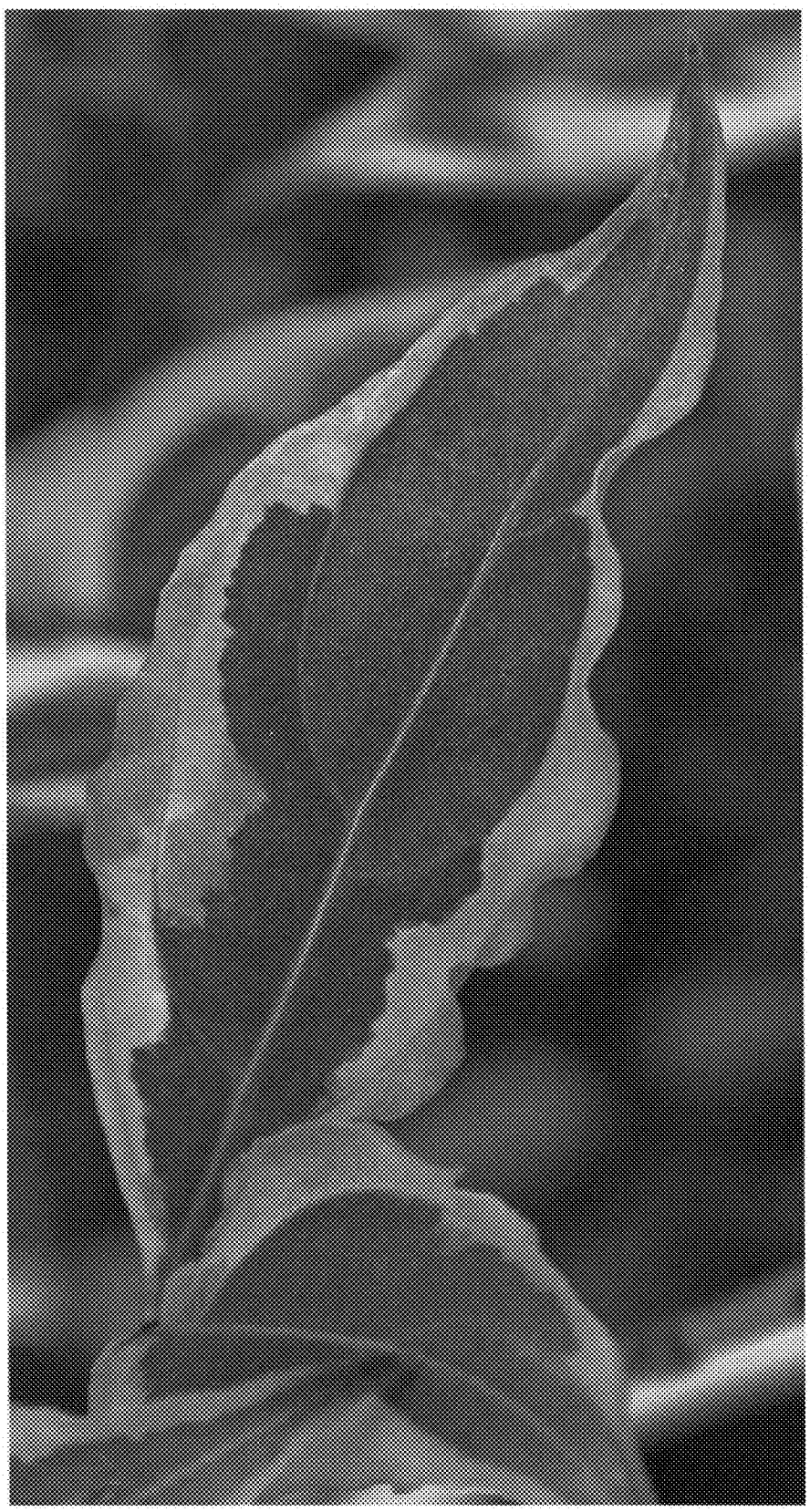

* * * * *